United States Patent [19]

Lawson

[11] Patent Number: 4,548,813
[45] Date of Patent: Oct. 22, 1985

[54] MEDICINAL EXTRACT OF THYMUS GLANDS

[76] Inventor: Rommon L. Lawson, Rte. 1, Box 33, China Spring, Tex. 76633

[21] Appl. No.: 460,609

[22] Filed: Jan. 24, 1983

[51] Int. Cl.⁴ ............................................. A61K 35/12
[52] U.S. Cl. ...................................................... 424/95
[58] Field of Search ......................................... 424/95

[56] References Cited

U.S. PATENT DOCUMENTS

| | | | |
|---|---|---|---|
| 3,438,859 | 4/1969 | Somer et al. | 424/95 |
| 3,466,367 | 9/1969 | Jaeger et al. | 424/95 |
| 3,657,417 | 4/1972 | Brunetti et al. | 424/95 |
| 4,128,637 | 12/1978 | Naylor et al. | 424/95 |
| 4,374,828 | 2/1983 | Folker et al. | 424/95 |

OTHER PUBLICATIONS

Pini et al.–Chem. Abst., vol. 77 (1972), p. 39,191c.
Recherche–Chem. Abst., vol. 63 (1965), p. 11263e.
Trainin–Chem. Abst., vol. 86 (1977), p. 111167e.
Yeshiva Univ.–Chem. Abst., vol. 73 (1970), p. 69833y.

*Primary Examiner*—Sam Rosen
*Attorney, Agent, or Firm*—Harvey B. Jacobson

[57] ABSTRACT

A medicinal extract of whole thymus glands for the treatment of animals suffering from immune related conditions is disclosed. The medicinal extract of thymus glands comprises a saline extract of ground whole thymus glands of chinchilla, bovine or sheep, injectable water and optionally a preservative. If frozen, the medicinal extract would also contain an antibiotic. The process for the preparation of the medical extract is disclosed. Additionally, a process of treating animals suffering from immune related conditions is also disclosed.

6 Claims, No Drawings

MEDICINAL EXTRACT OF THYMUS GLANDS

BACKGROUND OF THE INVENTION

This invention relates to a medicinal extract made from whole thymus glands of either chinchilla, bovine or sheep. This invention further relates to a method of preparing such an extract and a method of treating animals suffering from immune related conditions.

The thymus gland is involved with the immune system through its hormones and hormone-like factors including Metcalf's lymphocytosis-stimulating factor, Miller's competence including factor, homostatic thymus hormone, thymopoeitin I and II and thymosin. Although it is not known if these are the same substances under different names, it is known that individually these thymic substances have lymphocytopoietic effects, and can prevent both wasting disease and fatal virus infections in thymectomized mice. All thymectomized laboratory animals show a significant decrement in the immune response.

In addition, the thymus gland has an indirect effect on the immune system. Many lymphocytes, which are directly involved in the immune system, pass through the thymus. During the time these lymphocytes are in the thymus, the lymphocytes will differentiate and mature and are possibly influenced by thymic hormone-like factors. Thus, a mixed heterogenous population of thymus cells might control through its final products the hormonally conditioned mature lymphocytes and exert an indirect effect on the immune system.

The thymus gland is active from birth to puberty and then appears to atrophy and slough off its peripheral cells. The thymus gland effects the immune system even after it atrophies. The peripheral cells of the atrophied thymus gland migrate to form some of the reticuloendothelial tissues associated with the development of the immune responses in the adult by producing substances such as anti-bodies and interferon.

Each of the isolated thymic hormones and hormone-like factors have a specific function. The thymic medicinal extract herein described contains most or all of the thymic hormones and hormone-like factors. The totality of these hormones and factors work to stimulate the immune system to produce the theraputic results herein described.

An object of the present invention is to provide a medicinal extract made from whole thymus glands of either chinchilla, bovine or sheep which has a theraputic effect on the immune system that can produce the results herein described.

Another object of the present invention is to provide a method of preparing such a medicinal extract of thymus glands.

A further object of this invention is to provide a method of treating animals suffering from immune related conditions with the medicinal thymic extract.

SUMMARY OF THE INVENTION

This new medicinal extract of thymus gland for the treatment of animals comprises a saline solution of ground whole thymus glands of chinchilla, bovine or sheep, sterile injectable water and optionally a preservative. The medicinal extract of thymus gland may also contain an antibiotic to prevent bacterial contamination if the medicinal extract is to be frozen for storage. The method of preparing such an extract is described herein. Also described is a method of treating animals suffering from immune related conditions with this medicinal extract of thymus gland.

The thymus becomes nonfunctional at puberty. However, I have found that in chinchillas (fur-bearing rodents valued for its pelt), the thymus does not become nonfunctional at puberty but instead remains functional throughout this animal's lifespan. A medicinal extract made from chinchilla thymus will stimulate the immune response even in animals of different species. Such a medicinal chinchilla thymic extract is more effective than extracts made from other animals when treating animals of a different species. Medicinal extracts made from chinchilla thymus, cattle thymus or sheep thymus will stimulate the immune response when used in treating that same or different species.

Thymic hormones and hormone-like factors each affect the immune system. However, heretofore, an extract from the entire thymus gland has not been used as a theraputic agent. The thymic extract of the present invention contains most or all of the thymic hormones and factors together. The theraputic results obtained from the use of this extract made from whole thymus glands are impressive. Use of this thymic extract has resulted in dose related immune responses especially as to the IgG fraction when electrophoresis studies have been conducted. The thymic extract has reduced fever in animals, has caused improvement and complete recovery in animals suffering from demodectic mange, can improve the condition of animals suffering from mycoplasma (which is apparently an immune related disease), has been shown to be effective against stress in cattle, in treating feedlot "knockouts", treating sheep "non-doers" and treating polyarthristis in sheep. Thymic extract has also inhibited mammary tumors in animals and has caused weight gain in animals suffering from low body weight and in young animals suffering from stress.

DESCRIPTION OF THE PREFERRED EMBODIMENTS

The medicinal extract can be prepared from either chinchilla, bovine or sheep thymus glands. Basically the method of preparing the medicinal extract comprises homogenizing fresh whole thymus glands in saline, cooling the homogenate to an preselected cooling temperature, centrifuging the homogenate which had been cooled to remove particulate matter, saturating the homogenate in an amount of saline equal to the removed particulate matter, heating and agitating the resulting extract solution at a preselected heating temperature, removing any precipitate formed as a result of the heating, diluting and filtering the extract solution and adding a preservative, if needed.

It is preferred that fresh thymus glands are obtained in a frozen state and allowed to be thawed. The thymus glands are defatted and all extraneous facia and membranes are removed from the glands. The tissue can be ground in a meat grinder and then homogenized in saline e.g. 0.15 M NaCl. The preferred ratio of homogenized tissue to saline is 1 to 3 by weight.

The homogenate is cooled to a temperature range of 4° to 6° C., typically 5° C. The cooled homogenate is centrifuged to remove particulate matter. Typically, the cooled homogenate is centrifuged at approximately 2500xg for approximately 15 minutes at approximately 5° C. The removed particulate matter is replaced by an approximately equal volume of saline. The resulting solution is allowed to saturate from about 4 to 8 hours, typically 6 hours.

The resulting extract solution is then heated typically at 80° C. for approximately 20 minutes to form a precipitate. Acceptable heating temperatures range from 78° to 82° C. During heating, the extract solution is agitated until no more precipitate is formed.

While still warm the precipitate is removed. One way to remove the precipitate is by passing the extract solution through a sterile grease filter. The extract solution is thereafter diluted with sterile water. The amount of sterile water added is approximately equal to the amount of precipitate removed. The extract is allowed to cool to an acceptable cooling temperature between about 4° to 6° C. After cooling the extract is filtered through 0.45 μm pore size filter. A preservative is added if the extract is not to be used immediately. The preferred preservative is 0.75% benzyl alcohol.

The extract can be placed in serum bottles or lyophilized for storage. The medicinal thymic extract may be reconstituted by the addition of nonpyrogenic injectable water up to the original volume.

The medicinal thymic extract may also be frozen for storage. Before freezing, antibiotics are added to inhibit bacterial growth. The preferred antibiotics used are 0.25 gm of streptomycin sulfate and 250 I.U. pencillin G. potassium per 500 ml of extract. Alternatively, any acceptable antibiotic to control bacterial growth may be utilized. After the addition of the antibiotic, the pH of the extract is adjusted to about 6.8 with HCl or NaCl as needed. The extract is then passed through a millipore filter. The range of the pore size of the filter is 0.45μ to 0.22μ. This sterilizes the solution by filtration. The antibiotics and preservatives are precautionary measures against bacterial invasion during storage.

Nonlyophilized extract has a shelf life in excess of 2 years while lyophilized extract has a shelf life in excess of 4 years.

The amount of extract per dose will vary according to the species treated. Within each species the amount of extract per dose will further vary according to the body weight of the animal treated. When treating canines the dosage will range from 75 mg. to 200 mg. When treating cattle, the dosage will range from 125 mg. to 350 mg. When treating sheep the dosage will range from 25 mg. to 50 mg. Each dose is administered by an interperitoneal injection and repeated at two week intervals if necessary.

The dose equivalent amounts per injection of raw chinchilla thymus homogenate (C.T.H.) used in the animal studies in examples 1 to 3 was approximately 1.7 mg of chinchilla thymus extract (C.T.E.) in ¼ cc of physiological saline.

EXAMPLE 1

A study was conducted to determine the effects of varying doses of interperitoneal injections of bovine thymus extract and chinchilla thymus extract upon rats. No deleterious effects were ascertained. Hemotalogic differential counts did indicate a change in lymphocytes. Lymphocytes are involved in the immune response. Plasma electrophoresis and immune diffuse electrophoresis showed wide variation according to dose especially as to the IgG fraction which also indicates an immune response. This immune response produced by the thymic gland extract appears to be dose related.

Thymus Studies
Plasma Electrophoresis & Immuno-Diffusion

Chinchilla Thymus Extract - Serial Injected Animals
Plasma Electrophoresis - % Total Fraction = 100% IgG - Related to Pooled Sprague Dawley Rat Serum Standard; Standard Reference = 100%

Pre-Treatment: 1.6 mg. Chinchilla Thymus Extract (C.T.E.)/injected every 2 wks.
1.6 mg. = ¼ Chinchilla Thymus Gland = 1 equivalent dose.
1 equivalent dose Chinchilla Thymus Gland Homogenate (C.T.H.) = 0.023 grams Group Data

| Treatment Group | Treatment | # Animals | Plasma Electrophoresis % Fraction | | | | | |
|---|---|---|---|---|---|---|---|---|
| | | | γ | β | $a_2$ | $a_1$ | albumin | IgG |
| Pre-Treatment | | | | | | | | |
| C-1 | None | 4 | 9.8 | 25.7 | 12.8 | 16.0 | 35.7 | 64.9 |
| C-2 & C-5 | None (1 equiv C.T.E.) | 20 | 9.6 | 18.8 | 8.2 | 16.6 | 46.1 | 89.0 |
| C-3 & C-6 | None (2 equiv C.T.E.) | 12 | 9.8 | 23.4 | 9.1 | 14.4 | 43.4 | 86.2 |
| C-4 | None (3 equiv C.T.E.) | 10 | 11.1 | 20.3 | 8.1 | 13.4 | 47.1 | 109.6 |
| C-7 | None (2 equiv C.T.H.) | 2 | 9.2 | 23.4 | 12.1 | 16.4 | 38.9 | 82.0 |
| 4-Day Post Treatment | | | | | | | | |
| C-1 | None | 2 | 9.0 | 22.8 | 9.2 | 16.3 | 42.7 | 64.0 |
| C-2 & C-5 | 1 equiv C.T.E. | 11 | 11.2 | 20.1 | 9.9 | 16.9 | 42.0 | 119.8 |
| C-3 & C-6 | 2 equiv C.T.E. | 15 | 10.1 | 21.7 | 11.1 | 18.0 | 39.2 | 89.6 |
| C-4 | 3 equiv C.T.E. | 5 | 11.2 | 17.9 | 10.3 | 20.7 | 39.9 | 130.2 |
| C-7 | 2 equiv C.T.H. | 7 | 8.2 | 22.9 | 7.9 | 14.5 | 46.5 | 83.9 |
| 32-Day Post Treatment | | | | | | | | |
| C-1 | None | 9 | 8.7 | 21.6 | 6.5 | 16.3 | 46.8 | 98.3 |
| C-2 & C-5 | 1 equiv C.T.E. | 16 | 10.7 | 17.8 | 8.1 | 19.0 | 44.6 | 97.2 |
| C-3 & C-6 | 2 equiv C.T.E. | 15 | 9.2 | 19.0 | 9.0 | 17.3 | 45.7 | 86.3 |
| C-4 | 3 equiv C.T.E. | 6 | 11.6 | 16.6 | 9.0 | 20.2 | 42.6 | 112.0 |
| C-7 | 2 equiv C.T.H. | 7 | 9.2 | 21.8 | 7.9 | 13.8 | 47.3 | 81.0 |

EXAMPLE 2

The effects of varying doses of interperitoneal injections of chinchilla thymus extract upon rats that had DMBA (7,12-Dimethybenz [α]-anthracene) induced mammary tumors were studied. The spontaneous occurance of tumors in the absence DMBA in rats of the age used is approximately 50% as shown by others. The pre-treatment of chinchilla thymus extract on older rats resulted in a more pronounced response. Additional injections of chinchilla thymus extract after exposure to DMBA demonstrated a further protection against DMBA induced mammary tumors. This study has demonstrated that thymus extract has a dose related effect upon the inhibition of mammary tumors in rats.

to have effects upon lethargic mice as shown by the recorded 0% mortality rate as compared to the normal mortality rate of 81%.

TABLE 1

| | | | | # of mice | Mortality | | |
|---|---|---|---|---|---|---|---|
| | Phenotype | Type of | Dosage | receiving | Age of mice (days) | | % |
| Group | of mice | injection | (mg/ml) | injection | 15-24 | 25-34 | rate |
| I | Normal LH/+ | Liver homogenate | 0.5/0.15 | 21 | 0 | 0 | 0 |
| II | "Lethargic" lhlh | Liver homogenate | 0.5/0.15 | 20 | 0 | 8 | 40.0 |
| III | "Lethargic" lhlh | Thymus extract | 0.25/0.1 | 16 | 0 | 6 | 37.5 |
| IV | "Lethargic" lhlh | Thymus extract | 0.5/0.2 | 24 | 0 | 1 | 4.1 |

However, when subsequently comparing the effects

| Thymus Studies - Incident of Tumors - 40 Weeks Observation | | | | | | | |
|---|---|---|---|---|---|---|---|
| Old Animals | Old Animals Pre-treatment: | | | | Young Animals | | |
| Sprague Dawley Rats | Chinchilla Thymus Gland Extract (C.T.E.) | | | | Sprague Dawley Rats | | |
| Pre-treatment age 91 days | or Chinchilla Thymus Gland Homogenate | | | | Experiment age 100 days | | |
| Experiment age 276 days | (C.T.H.) given every two weeks for 3-4 | | | | (approximately) | | |
| Termination age 541 days | weeks in varying doses (equivalents) | | | | Termination age 356 days | | |
| | 1 equiv. dose = 1.6 mg. C.T.E. or 0.023 grams | | | | | | |
| | C.T.H. = ½ of raw chinchilla thymus gland | | | | | | |
| | Group | Treatment | | | | | |
| Experiment: | I | Control | | | | | |
| | II | D.M.B.A. only (Positive Control) Old Animals | | | | | |
| | II | D.M.B.A. only (Positive Control) Young Animals | | | | | |
| | II | D.M.B.A. + Pre-treatment | | | | | |
| | III | D.M.B.A. Initially + 3 mg. C.T.E. and 3 mg. C.T.E. every 3 weeks for 40 weeks | | | | | |

| Group | Animals Old or Young | Pre-Treatment | Experimental Treatment | #Animals | #Tumor Animals | % Tumors | Pathology Ave. Group Tumors Grade | Adjusted % (−) Control 50% |
|---|---|---|---|---|---|---|---|---|
| I | Old | None | Control | 8 | 4 | 50 | 1.42 | 00 |
| II | Old | None | D.M.B.A. Positive Control | 5 | 5 | 100 | 2.75 | 50 |
| II | Young | None | D.M.B.A. Positive Control | 15 | 11 | 73 | 1.78 | 23 |
| II | Old | C.T.E. | D.M.B.A. | 39 | 20 | 51 | 1.44 | 01 |
| Subgroup: | (a) 1 equiv C.T.E. - 3 inj | | | 5 | 0 | 00 | 0.00 | −50 |
| | (b) 2 equiv C.T.E. - 3 inj | | | 10 | 5 | 50 | 2.75 | 00 |
| | (c) 3 equiv C.T.E. - 3 inj | | | 5 | 5 | 100 | 1.00 | 50 |
| | (d) 1 equiv C.T.E. - 4 inj | | | 5 | 2 | 40 | 2.75 | +10 |
| | (e) 2 equiv C.T.E. - 4 inj | | | 9 | 6 | 67 | 0.88 | 17 |
| | (f) 2 equiv C.T.H. - 4 inj | | | 5 | 2 | 40 | 1.00 | −10 |
| III | Old | C.T.E. | D.M.B.A. + C.T.E. | 14 | 6 | 43 | 1.33 | −07 |
| Subgroup: | (a) 1 equiv C.T.E. - 3 inj | | | 5 | 4 | 80 | 1.33 | 30 |
| | (b) 1 equiv C.T.E. - 4 inj | | | 4 | 2 | 50 | 1.00 | 00 |
| | (c) 2 equiv C.T.H. - 4 inj | | | 5 | 0 | 00 | 0.00 | −50 |
| III | Young | None | D.M.B.A. + C.T.E. | 15 | 9 | 60 | 2.38 | 10 |

Pathology Legend:
0 = None
1 = Benign
2 = Low Malignancy
3 = Medium Malignancy
4 = High Malignancy

EXAMPLE 3

This study was conducted to determine the effects of interperitoneal injections of chinchilla thymus extract on an inbred strain of "lethargic" mutant mice (BALB/CGN). These mice have a high mortality rate and a great loss of body weight during early stages of life. A total of ten injections were administered to each mouse. The first injection was given at age 15 days. This was followed by three injections per week over a three-week period. It has been suggested that the mutant genes of these mice are related to spontaneous thymic involution. These lethargic mice suffer from an immune deficiency. Chinchilla thymic extract was demonstrated to have effects upon lethargic mice as shown by the recorded 0% mortality rate as compared to the normal mortality rate of 81%.

of chinchilla and bovine thymic extracts on lethargic mice, it was found that chinchilla thymic extract resulted in more pronounced regrowth of the thymus upon post mortem examination and a better weight gain response than the bovine thymic extract. In this case, the chinchilla thymic extract was preferred.

EXAMPLE 4

A licensed veterinarian was treating a calf suffering from an unknown ailment for three weeks without apparent success. The veterinarian suspected the cause of the calf's illness was of an immune nature. The calf was then treated with 200 mg. of chinchilla thymus gland extract prepared four years earlier. The extract was administered in 20 cc of injectable water in one interperitoneal injection. The calf received no further treatment of any kind. Within three days of the medicinal thymus extract treatment, the veterinarian pronounced the calf well.

EXAMPLE 5

A calf suffering from high fever complicated by nasal discharge of pulmonary origin had been treated by a licensed veterinarian for three days without success. The calf was administered one interperitoneal injection of 175 mg of lyophilized bovine thymus gland extract (prepared four years earlier) in 25 cc. of injectable water. Within twenty four hours, the calf's temperature was normal and the nasal discharge had ceased. At seven days post treatment the calf had reestablished normal eating behavior and appeared normal in all respects.

EXAMPLE 6

A Dachshund puppy was suffering from immune related demodectic mange. Lesions covered ⅔ of the dog's body. In the past, medication has not been effective in the treatment of this condition resulting in the extermination of most affected animals. The dog was given one interperitoneal injection every two weeks of 75-100 mg. of chinchilla thymus extract (prepared several years earlier) in 15 cc. of injectable water. Within two weeks, the veterinarian prounouced the dog better. After six weeks the veterinarian claimed the prognosis for complete recovery looked good. The lesions were healing and new hair was growing. Treatment stopped after the third injection since no more chinchilla thymus extract was available. After a six month post treatment follow-up, the veterinarian pronounced the dog completely cured.

EXAMPLE 7

A 64 lb. Doberman pinscher dog diagnosed as suffering from demodictic mange did not respond to any medication. Lesions covered most of the dog's body. The dog was treated with one interperitoneal injection every two weeks for the next six weeks. The injection was 25 cc of freshly prepared chinchilla thymus extract in solution containing approximately 190 mg of thymus protein. After two weeks, the lesions were healed. By the fourth week, new hair had grown over the affected areas. After a six month post treatment follow-up the dog was completed recovered.

EXAMPLE 8

A 126 lb. great dane dog was suffering from immune related demodectic mange and other immune related disorders. Approximately ⅔ of the dog's body was affected. Several weeks of conventional medical treatment had produced no results. Although the owner wanted to destroy the dog, the dog was referred for experimental treatment. The dog was administered one interperitoneal injection of 25 cc (190 mg thymus protein) of chinchilla thymus gland extract. After two weeks, the dog was somewhat improved. Due to the amount of scratchng by the dog, the veterinarian increased the dosage to ¼ cc. per pound of body weight. After an additional week, the dog's condition was markedly improved. However, the owner decided to have the dog destroyed even though the veterinarian felt that the dog would recover completely given time.

EXAMPLE 9

A chihuahua dog was diagnosed as suffering from demodectic mange that was resistant to conventional medication. The dog was treated with one interperitoneal injection of ¼ cc. per pound of body weight (1.9 mg of thymus protein per pound) of chinchilla thymus gland extract. After two weeks there was a marked improvement. A second injection was administered. The owner never returned the dog for additional treatments.

EXAMPLE 10

A 13 lb. toy poodle dog was suffering from re-occurring mammary tumors. These tumors had for several years been removed surgically approximately every six months by a veterinarian. The dog was treated with one interperitoneal injection of 13 cc. (approximately 98 mg) of chinchilla thymus extract after the surgical removal of the mammary tumors. One year later the dog's owner had not brought the dog back for any further removal of mammary tumors.

EXAMPLE 11

A 13 yr. old miniature female schnauzer dog had 10-15 mammary tumors of various sizes. These tumors re-occurred periodically and had to be surgically removed each time. The veterinarin advised against continued surgery due to the age of the dog. The dog was treated by injecting about 2 cc. of chinchilla thymus gland extract interperitoneally and by injecting the extract into and about each tumor. The dose was varied according to the size of each tumor. Several treatments were administered at two week intervals. After several weeks the small tumors totally regressed while the large tumors regressed only partially.

EXAMPLE 12

Two goats were suffering from mycoplasma, which is of an immune related nature. The symptoms of mycoplasma are swelling of the joints, general arthristis, and chronic respiratory involvement. Each goat received one interperitoneal injection of 30 cc. (approximately 25 mg) of bovine thymus gland extract. As a result, the swelling of the joints regressed and the goats appeared normal for about six months. It is felt that a series of such treatments would cause greater improvement.

EXAMPLE 13

This experiment was conducted on "knock-out" animals. As used herein, knock-out animals are defined as animals that are hauled a great distance, given a series of medications, kept in crowded confinement, branded and often de-horned and castrated, and as a result do not eat very well and demonstrate a weight loss. These animals usually get sick and are removed to the sick pen and given a broad spectrum of antibiotics. This happens to animals in feed lots. Knock-outs usually never go back on feed or do well in the feed lots. The majority of them die. As the animals were purchased from the feed lots, they were given a grade according to their condition, 0 to 4.

Grade 0—no apparent illness, not eating well
    1—showing signs of stress, will not eat well
    2—noticeably sick, becoming thin
    3—sick, thin, will not eat, slight fever, beginning to demonstrate some respiratory trouble 4—very sick, fever, thin, will not eat, mucous running from the nose, respiratory trouble, unsteady on feet Seventy-eight calves were purchased with the following grades of sickness:

| | |
|---|---|
| 6 | Grade 4 |
| 19 | Grade 3 |
| 12 | Grade 2 |
| 9 | Grade 1 |
| 32 | Grade 0 (11 of grade 0 were not treated) |
| 78 | Total |

The 78 calves were given between 40 and 60 cc. of bovine thymus gland extract interperitoneally, depending on body weight ($\frac{1}{8}$ cc. per pound). There was marked improvement in all the calves on about the 7th to 9th day post-treatment. They began to consume feed and have a steady weight gain. After a few months on feed, they were sold at the regular auction sale barn. Eleven animals out of the group died, of which three calves had hardware disease and three calves had some other malady unrelated to the immune system.

It was concluded that the animals that are placed in a sick pen at the feed lot are given such massive doses of antibiotics that they are almost beyond help. However, the bovine thymus gland extract was highly successful in treating approximately 80% of the animals purchased. It would have been preferred to give the bovine thymus gland extract to these animals at the onset of the stress condition without the use of antibiotics.

EXAMPLE 14

This experiment was conducted on non-doer animals. As used herein, "non-doers" are defined as lambs on feed that do not eat very well, do not gain weight and are stunted compared to their peers. They eventually die or are culled out of the feed lot program. This represents quite a monetary loss to the owner of the animals. The purpose of this experiment is to stimulate the animals' immune systems in such a manner so as to restore their emmaciated condition and cause them to go back on feed.

Each lamb was given 5 cc. of sheep thymus gland extract interperitoneally. The animals weighed between 30 to 60 pounds. Within three days the animals started to improve and begin to eat and drink, to show healthy activity, and had bright eyes. Within a week, the animals appeared normal. Within two weeks they demonstrated a marked increase in weight gain over their peers.

EXAMPLE 15

Five non-doer lambs were each given 5 cc. of sheep thymus gland extract interperitoneally. Five normal lambs were used as controls and received no treatment. Both groups were observed for weight gain. After three days, the non-doer lambs began to eat normally and gain weight. By the second week the non-doers' weight gain equaled the controls' weight gain. By the third week, the non-doer animals exceeded the control group in weight gain. All animals were then returned to the regular feed lot pens.

EXAMPLE 16

Fifteen non-doer sheep were treated with interperitoneal injections of 5 cc. of sheep thymus gland extract. Three days after treatments the non-doer sheep were eating and drinking. Three weeks later these animals were apparently normal, were eating and gaining weight and had glossy coats.

EXAMPLE 17

This experiment was conducted on young calves suffering from stress. These animals are stressed from being weaned too young, hauling, crowded conditions and summer heat. Often the death loss is tremendous within a few months due to this stress condition. The following experiment was conducted on such young stressed calves:

15—control animals, no treatment
16—animals injected with 25 cc. of sheep thymus gland extract interperitoneally
15—animals injected with 25 cc. of bovine thymus gland extract interperitoneally After 30 days, several of the control group appeared severely stressed and died. This degree of loss was expected. The treatment groups were eating and gaining weight. Only one animal was lost from the treatment groups. This animal was emmaciated and weak at the time of treatment. All the other 30 animals in the treatment groups survived.

EXAMPLE 18

In a pre-conditioning feed lot, four calves were down from trauma. These animals suffered from trauma due to being hauled for some distance, unloaded, run through a chute, branded, castrated, given shots and sometimes dehorned, all in one operation. Animals suffering from such trauma often do not recover. These four calves were treated with one interperitoneal injection of 200 mg. of bovine thymus gland extract (prepared four years previously) in 25 cc. of injectable water. The next day the calves were up and eating. Within ten days, they were back on the regular feed lot regime and appeared completely normal.

EXAMPLE 19

Five sheep suffering from polyarthritis were each given 5 cc of sheep thymus gland extract interperitoneally. Five healthy sheep were used as controls and were treated identically. The day following treatment the five polyarthritic sheep were on their feet (previously they could not get up) and were eating normally. The control sheep also appeared completely normal. Three weeks later the sheep were put in the fattening sheep feed lot.

The amount of extract per dose will vary according to the species treated, and the body weight of the animal treated.

DOSAGE RANGE

Canine

Chinchilla or bovine extract—
75 to 100 mg.—up to 15 pounds body weight
125 mg.—15-25 pounds body weight
150 mg.—25-50 pounds body weight
200 mg.—over 50 pounds body weight Administered interperitoneally, every two weeks, if necessary.

Bovine

Chinchilla, bovine or sheep extract—
125 mg.—up to 100 pounds body weight
200 mg.—100-400 pounds body weight 250 mg.—400–500 pounds body weight
350 mg.—over 600 pounds body weight
Administered interperitoneally, every two weeks, if necessary.

Sheep

Chinchilla, bovine or sheep extract—
25 mg.—up to 50 pounds body weight
35 mg.—50–100 pounds body weight
50 mg.—over 100 pounds body weight
Administered interperitoneally, every two weeks, if necessary.

As will be readily understood by those of ordinary skill in the art, minor modifications may be made in the invention described above without in any way departing from the spirit and scope of the invention. Accordingly, it is understood that the invention will not be limited to the exact details disclosed hereinabove, but will be defined in accordance with the appended claims.

What is claimed is:

1. A medicinal extract of thymus gland for the treatment of animals comprising an effective amount of a saline extract of ground whole thymus gland of chinchilla free of heat-precipitable impurities and injectable water.

2. A medicinal extract of thymus gland as recited in claim 1 further comprising a preservative.

3. A medicinal extract of thymus gland as recited in claim 1 further comprising an antibiotic.

4. A process for the preparation of the medicinal extract of thymus gland as recited in claim 1 comprising:
   homogenizing fresh ground whole thymus gland of chinchilla in saline;
   cooling the homogenate to a cooling temperature of 4°–6° C.;
   centrifuging the cooled homogenate to remove particulate matter;
   saturating the homogenate in an amount of saline equal to the removed particulate matter;
   saturating the homogenate in an amount of saline equal to the removed particulate matter;
   heating and agitating the resulting extract solution at a heating temperature of 78°–82° C.;
   removing any precipitate formed;
   diluting the extract solution;
   filtering the extract solution;
   adding an antibiotic; and
   adjusting the pH of the resulting extract solution.

5. An injectable preparation containing from about 25 to 350 milligrams of the medicinal extract of thymus gland of chinchilla as recited in claim 1.

6. A process for the treatment of immune related diseases and reticulo-endothelial related diseases in animals which comprises administering an effective amount of the injectable preparation as recited in claim 5.

* * * * *